(12) United States Patent
Mikkaichi et al.

(10) Patent No.: US 7,534,248 B2
(45) Date of Patent: May 19, 2009

(54) ANASTOMOSING INSTRUMENT (75) Inventors: Takayasu Mikkaichi, Tokyo (JP); Keita Suzuki, Tokyo (JP)

(73) Assignee: Olympus Corporation, Tokyo (JP)

( * ) Notice: Subject to any disclaimer, the term of this patent is extended or adjusted under 35 U.S.C. 154(b) by 397 days.

(21) Appl. No.: 10/859,849

(22) Filed: Jun. 3, 2004

(65) Prior Publication Data
US 2004/0249392 A1 Dec. 9, 2004

(30) Foreign Application Priority Data
Jun. 6, 2003 (JP) .............................. 2003-162009

(51) Int. Cl.
*A61B 17/04* (2006.01)
(52) U.S. Cl. ..................... 606/144; 606/151; 606/232
(58) Field of Classification Search ................ 606/232, 606/139, 144, 148, 151
See application file for complete search history.

(56) References Cited

U.S. PATENT DOCUMENTS

| | | | | |
|---|---|---|---|---|
| 3,961,632 A | * | 6/1976 | Moossun ..................... 604/528 |
| 4,235,238 A | * | 11/1980 | Ogiu et al. .................. 606/145 |
| 5,021,059 A | * | 6/1991 | Kensey et al. ................ 606/213 |
| 5,041,129 A | * | 8/1991 | Hayhurst et al. ............. 606/232 |
| 5,269,809 A | * | 12/1993 | Hayhurst et al. ............. 606/232 |
| 5,330,442 A | * | 7/1994 | Green et al. ................. 606/232 |
| 5,405,359 A | * | 4/1995 | Pierce ......................... 606/232 |
| 5,464,426 A | | 11/1995 | Bonutti |
| 5,470,337 A | * | 11/1995 | Moss .......................... 606/139 |
| 5,665,109 A | * | 9/1997 | Yoon ........................... 606/232 |
| 5,725,556 A | | 3/1998 | Moser et al. |
| 5,810,848 A | * | 9/1998 | Hayhurst .................... 606/144 |
| 5,879,371 A | | 3/1999 | Gardiner et al. |
| 6,056,760 A | | 5/2000 | Koike et al. |
| 6,068,648 A | * | 5/2000 | Cole et al. ................... 606/232 |
| 6,071,292 A | * | 6/2000 | Makower et al. ............ 606/158 |
| 6,074,409 A | * | 6/2000 | Goldfarb ..................... 606/232 |
| 6,319,271 B1 | | 11/2001 | Schwartz et al. |
| 6,491,707 B2 | * | 12/2002 | Makower et al. ............ 606/157 |
| 6,635,073 B2 | * | 10/2003 | Bonutti ....................... 606/232 |
| 6,699,263 B2 | * | 3/2004 | Cope ........................... 606/232 |
| 6,997,189 B2 | * | 2/2006 | Biggs et al. .................. 128/898 |
| 7,087,073 B2 | * | 8/2006 | Bonutti ....................... 606/232 |
| 2003/0191497 A1 | | 10/2003 | Cope |

FOREIGN PATENT DOCUMENTS

JP 59-21775 6/1984

(Continued)

*Primary Examiner*—Darwin P Erezo
(74) *Attorney, Agent, or Firm*—Scully, Scott, Murphy & Presser, P.C.

(57) ABSTRACT

The present invention aims to provide an anastomosing instrument that can anastomose biological tissue with surety.

This anastomosing instrument has an inserted portion, which is inserted into a body cavity and is provided with a puncture needle, and a hand-operated portion, which the surgeon operates from outside the body. This anastomosing instrument is designed as follows. Namely, an anchoring member for anchoring in biological tissue and a locking member for fastening on a suture material are housed inside the puncture needle. A first pushing member, for pushing the locking member out from the puncture needle ahead of the anchoring member, and a second pushing member, for pushing the anchoring member out from the puncture needle are passed through from the hand-operated portion.

3 Claims, 8 Drawing Sheets

FOREIGN PATENT DOCUMENTS

| | | |
|---|---|---|
| JP | H10-211206 | 8/1998 |
| JP | 2000-501638 | 2/2000 |
| JP | 2000-225118 | 8/2000 |
| JP | 2001-507972 | 6/2001 |
| JP | 2002-191608 | 7/2002 |

* cited by examiner

ANASTOMOSING INSTRUMENT

BACKGROUND OF THE INVENTION

1. Field of the Invention

The present invention relates to an anastomosing instrument that is introduced into a body cavity via the channel of an endoscope.

This application is based on Japanese Patent Application No. 2003-162009, the contents of which are incorporated herein by reference.

2. Description of the Related Art

Procedure instruments that are inserted into a body cavity and are for suturing biological tissue in order to accomplish hemostasis, for example, are conventionally known. These types of procedure instruments have a puncture needle that can pass through biological tissue, and have a design wherein a suture pull-out preventing tip and fixture are housed in order from the end of the puncture needle (See Japanese Utility Model Application, Second Publication No. 59-21775 (page 3, FIGS. 14 and 23)).

In this kind of procedure instrument, the puncture needle is passed through two biological tissues that are to be anastomosed, and the pull-out preventing tip is pushed out from the puncture needle first. The fixture is subsequently pushed out of the puncture needle once the puncture needle is pulled out from the two biological tissues. Finally, the suture material is pulled, anastomosing the two biological tissues, which are then held with the fixture. As examples of fixtures, devices have been disclosed that house a tapered elastic fastening member inside a member having a tapered cavity, and hold the suture by means of the frictional force between these two members.

SUMMARY OF THE INVENTION

The first aspect of the invention is an anastomosing instrument in which an anchoring member, that is attached to one end of a suture material and is for anchoring in a biological tissue, and a locking member, through which the other end of the suture material is inserted and that comes into contact with the anastomosed biological tissue to function to prevent pull-out of the suture, are housed inside a puncture needle, wherein, once the puncture needle has passed through the biological tissue, the suture material is passed through the biological tissue as the anchoring member and the locking member are pushed out in accordance with operations from a hand held portion, thereby anastomosing the biological tissues; this anastomosing instrument characterized in that the locking member is disposed in the internal cavity of the puncture needle so that the surface of the locking member that is in contact with the biological tissue will be parallel to the axial direction of the puncture needle, and in the provision of a first pushing member that pushes out the locking member from the puncture needle and a second pushing member that is housed inside the first pushing member and pushes out the anchoring member from the puncture needle.

The second aspect of the invention is characterized in that, in the anastomosing instrument of the first aspect, the locking member and the anchoring member are disposed in this order from the end of the puncture needle, lying along the longitudinal direction of the puncture needle.

The third aspect of the invention is characterized in that, in the anastomosing instrument of the first aspect, the locking member has two bent pieces that are inclined with respect to its base so as be opposite one another, wherein these bent pieces are designed so that a suture material that was passed between the ends thereof is fastened when a force is applied to close the space between the opposing ends, and the fastening of the suture material is released when a force is applied to widen the space between the opposing ends.

The fourth aspect of the invention is characterized in that an anastomosing instrument of the first aspect is designed to have a flow introducing portion provided on the hand-held side for supplying flow to the puncture needle, and for gas to be discharged from the end of the puncture needle.

BRIEF DESCRIPTION OF THE DRAWINGS

FIG. 4 is a view showing the locking member, with FIGS. 4A, 4B and 4C being perspective, development elevation and cross-sectional views, respectively.

FIG. 8 is a view showing the locking member, with FIGS. 8A and 8B being front and perspective views, respectively.

FIG. 9 is a view showing the locking member, with FIGS. 9A and 9B being front and perspective views, respectively.

PREFERRED EMBODIMENTS OF THE INVENTION

Figure 1:
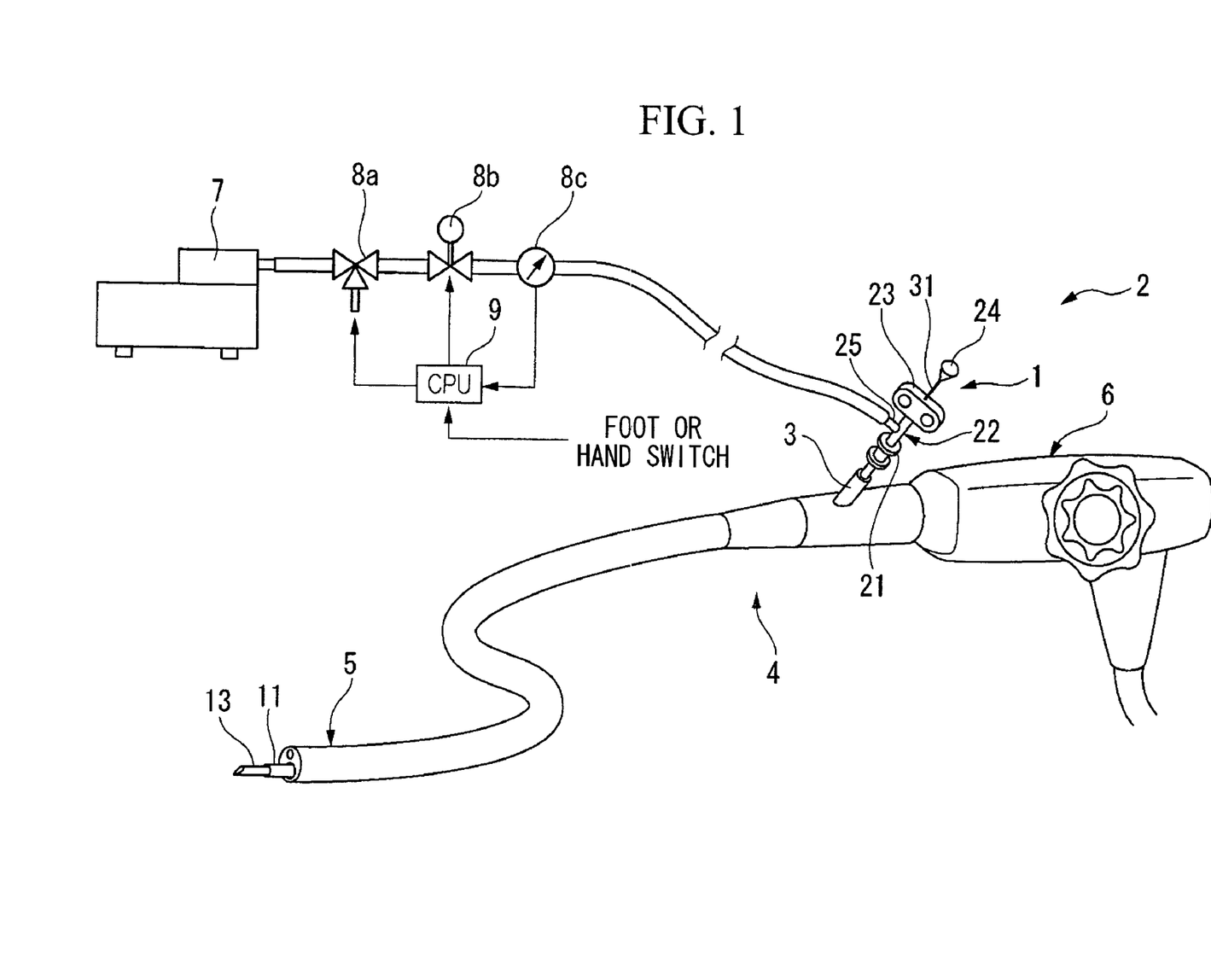
FIG. 1 is a schematic view of an endoscope treatment device that includes the anastomosing instrument according to the present invention.
Figure 2:
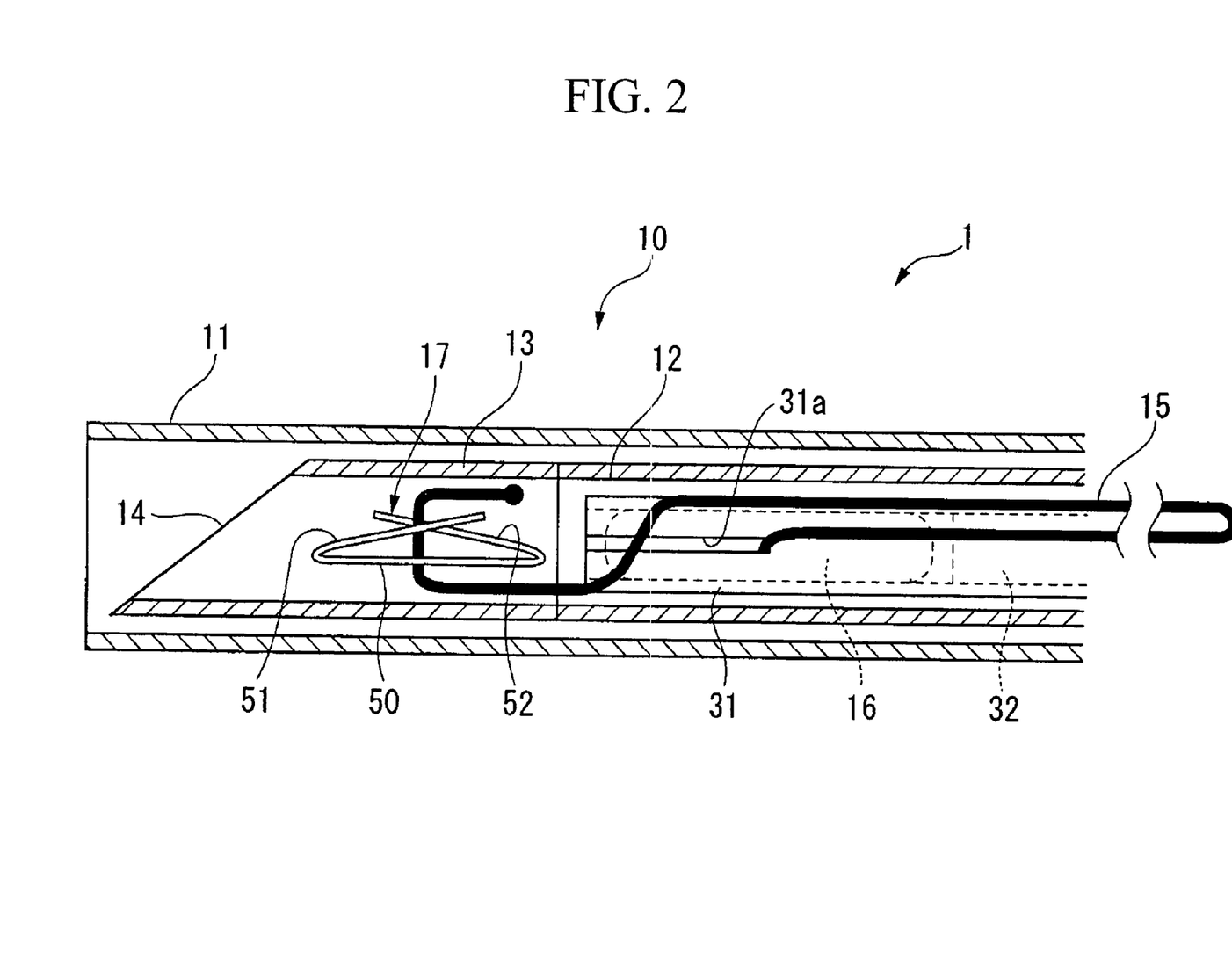
FIG. 2 is a cross-sectional view showing in the main the structure of the inserted portion of the anastomosing instrument.
Figure 3:
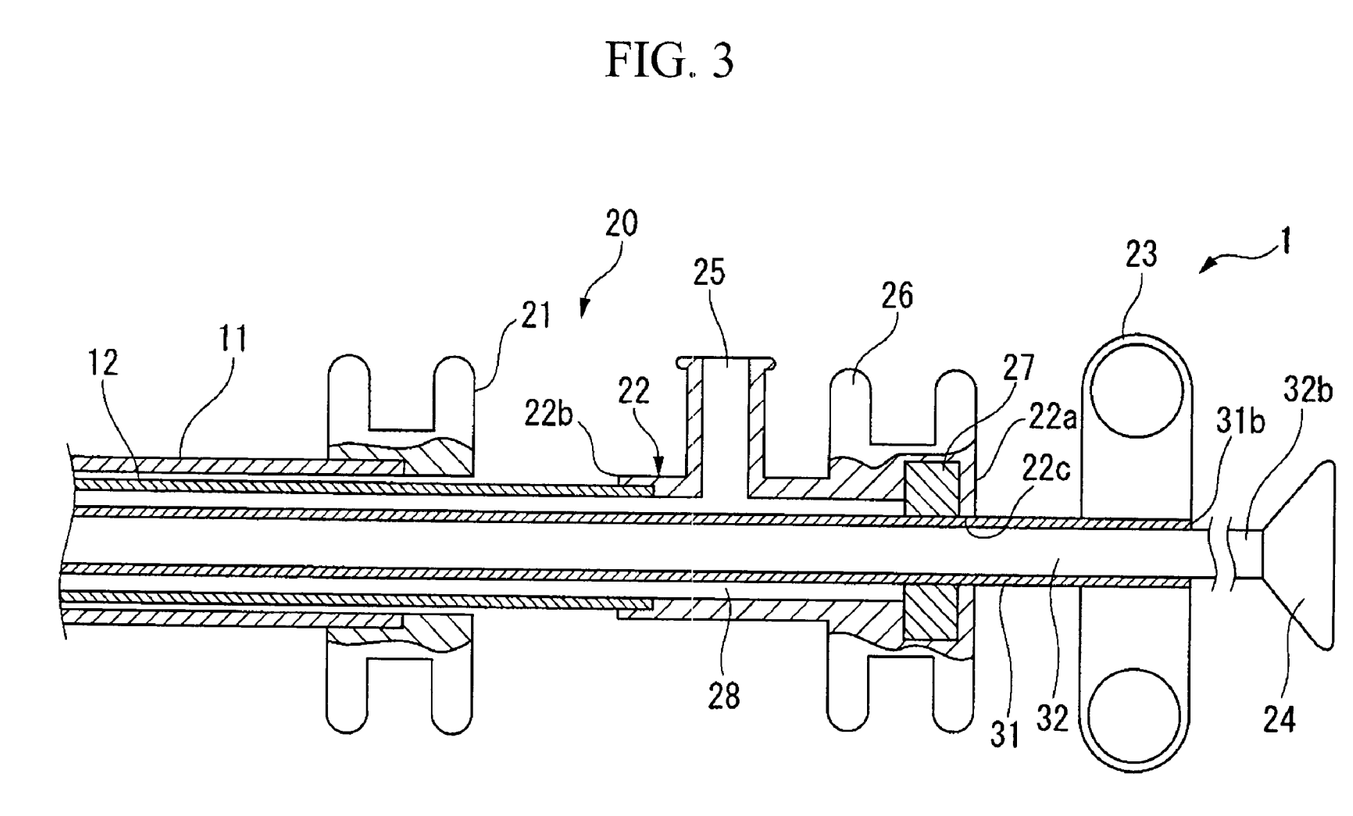
FIG. 3 is a cross-sectional view showing in the main the structure of the hand operated portion of the anastomosing instrument.

Embodiments of the present invention will now be explained in detail with reference to the figures. FIG. 1 is a schematic view of an endoscope treatment device that includes the anastomosing instrument according to the present embodiment. FIG. 2 is a cross-sectional view showing the inserted portion of the anastomosing instrument. FIG. 3 is a cross-sectional view showing in the main the hand-operated portion of the anastomosing instrument.

As shown in FIG. 1, the present embodiment's anastomosing instrument 1 is employed by insertion into the forceps channel 3 of endoscope treatment device 2. Endoscope treatment device 2 consists of an endoscope 4 into which anastomosing instrument 1 is inserted, and an air pump 7 which is the flow supplying means for supplying a gas such as air, i.e., the flow, to anastomosing instrument 1. Endoscope 4 consists of introduced portion 5 that is introduced into the body cavity and which has a forceps channel 3, illumination and a camera lens, etc. at one end thereof, and an operating portion 6 for operating introduced portion 5 from outside the body cavity.

As shown in FIGS. 2 and 3, anastomosing instrument 1 has a pliable inserted portion 10 that is inserted into a body cavity, and a hand-operated portion 20 which the surgeon operates from outside the body, and is designed so as to permit insertion and passage of pushing members 31, 32 internally.

Inserted portion 10 has an outer sheath 11, which is a flexible tube, an inner sheath 12 that is housed inside outer sheath 11 in a manner to permit its advance or withdrawal, and a puncture needle 13 that is attached to the end of inner sheath 12. The end of puncture needle 13 is beveled at an acute angle to form a sharp point, thus facilitating penetration into biological tissue. Puncture needle 13 has a hollow form in which the pointed end thereof has an opening 14, and an anchoring member 16 and a locking member 17, which are attached to suture material 15, are housed internally.

Figure 4A:
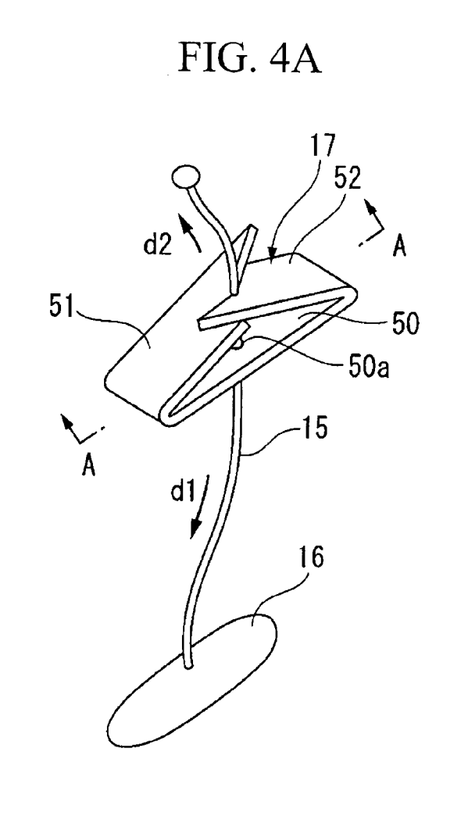

As shown in FIGS. 2 and 4A, anchoring member 16 consists of a cylindrically-shaped member. One end of suture material 15 for passing through biological tissue is anchored near a center point along the longitudinal direction of anchoring member 16. During anastomosis, anchoring member 16 comes into contact with the biological tissue in the wide area of its longitudinal direction, and is anchored in the biological tissue, thus preventing suture material 15 from being pulling out from the biological tissue. As a result of this type of shape and function, anchoring member 16 is sometimes referred to as a T-anchor or T-bar.

Figure 4B:
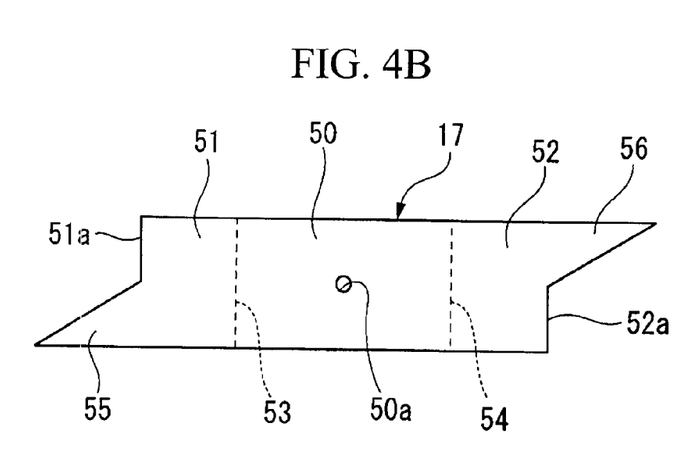

Locking member 17 functions to prevent suture material 15 from pulling out after anastomosis. Locking member 17 has two bent pieces 51,52 that rise from base 50 at a specific angle and so as to oppose one another. The other end of suture material 15 which is pulled out from anchoring member 16 is pulled through a hole 50a in base 50 and is passed between bent pieces 51,52. As shown in perspective view 4A and development elevation 4B, there is a hole 50a for passing the suture material that is formed in the center of the plate-shaped part of this locking member 17, and this locking member 17 has bent pieces 51,52, that are formed by bending the ends in the same direction and along bending lines 53,54 that are provided at specific positions on the long side of the plate-shaped part, and a base 50, which has a contact surface in which the portion having hole 50a comes into contact with the biological tissue. The distance between end 51a of bent piece 51 and end 52a of bent piece 52 may be set so that when there is no suture material 15 present, ends 51a and 52a are in contact with one another, or are separated by a distance that is less than the diameter of suture material 15.

Figure 4C:
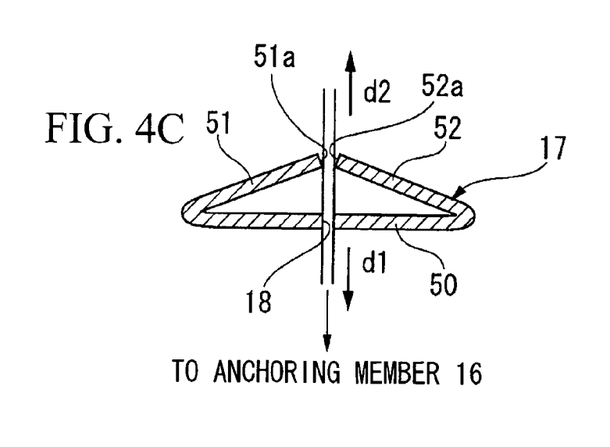

As shown in FIG. 4C, which is a cross-sectional view taken along the line A-A in FIG. 4A, when the other end of suture material 15 is passed through from base 50 to ends 51a,52a by widening the space between end 51a and end 52a, there is a force generated on bent pieces 51,52 to bring them closer together. Accordingly, if suture material 15 is pulled in the direction d1 toward base 50, ends 51a,52a also move in direction d1, causing the distance between ends 51a,52a to narrow. This fastens and locks suture material 15 in place, and prevents its movement. In other words, in the case where there is a force working on suture material 15 that will pull apart anchoring member 16 and locking member 17, locking member 17 is moved in a way that closes the space between ends 51a and 52a, and functions to lock movement of suture material 15. To restate, even if the target of anastomosis that is held between locking member 17 and anchoring member 16 pushes locking member 17 in the direction d2 toward the other end of suture material 15, ends 51a,52a fasten on suture material 15, and the position of locking member 17 with respect to suture material 15 is locked. Therefore, locking member 17 cannot be made to move in the direction d2.

On the other hand, when suture material 15 is pulled in direction d2 which is opposite base 50, ends 51a and 52a also move in direction d2 (i.e., a direction which moves them away from each other). As a result, their fastening on suture material 15 is released. In other words, movement of suture material 15 is permitted in the direction which brings anchoring member 16 and locking member 17 closer to one another. To restate, when locking member 17 is pushed toward the tissue to be anastomosed, i.e., when locking member 17 is moved in direction d1 toward the one end of suture material 15, the space between end 51a and end 52a widens, and the fastening of ends 51a,52a on suture material 15 is released. As a result, locking member 17 can move in direction d1.

Guide pieces 55,56 are provided extending from bent pieces 51,52 and are for stabilizing and holding suture material 15 in the middle thereof. Guide pieces 55,56 are triangular in shape and are provided with ends 55a,56a that are inclined and extend from the center point of the short sides of the plate-shaped part diagonally to a line that extends from the long sides of the plate-shaped part in FIG. 4B. Guide pieces 55 and 56 are formed at positions that are symmetrical about a point centered on hole 50a. Thus, as shown in FIG. 4A, even if guide pieces 55 and 56 are bent in this manner so as to bring bent pieces 51,52 closer together, they do not create an interference. Inclined ends 55a,56a guide suture material 15 so as to stably position it at the center of locking member 17. Thus, pulling out of suture material 15 from between bent pieces 51,52 during the anastomosing procedure is eliminated.

By positioning locking member 17 closer to the end of puncture needle 13 than anchoring member 16 in this embodiment, it is possible to employ a locking member 17 having a larger outer shape than anchoring member 16. Further, since base 50 of locking member 17 is disposed so as to be parallel to the long direction (axial direction) of puncture needle 13, the area of base 50 that is in contact with the biological tissue, i.e., the area of contact, can be secured at a maximum limit, even in the limited housing space within puncture needle 13.

One end of suture material 15 is fixed in place in anchoring member 16, and, as an end treatment, the other end of suture material 15 is tied into the shape of a ball. This end treatment is carried out after locking member 17 is inserted in a slidable manner, and has the function of preventing falling out of locking member 17 and facilitating gripping by other forceps. Other examples of end treatments that can be cited include tying the end of suture material 15 into the shape of a ring, or dissolving the end to form it into a clump.

As shown in FIGS. 2 and 3, the pushing member for pushing anchoring member 16 and locking member 17 out from puncture needle 13 consists of a first pushing member 31 for pushing out locking member 17 ahead of anchoring member 16, and a second pushing member 32 for pushing out anchoring member 16, and is inserted from the hand-operated portion 20 side until it reaches the inner sheath 12 and puncture needle 13. First pushing member 31 consists of a pipe having an outer diameter that is smaller than the inner diameter of puncture needle 13, and houses second pushing member 32 and anchoring member 16 internally in a slidable manner. For this reason, a slit 31a is provided to the end portion of first pushing member 31 from which suture material 15, which is attached to anchoring member 16, is pulled out. Note that it is preferable to provide a clearance sufficient to enable gas flow between first pushing member 31 and the inner wall of puncture needle 13.

The hand operated portion 20 shown in FIG. 3 consists of a holding member 21 that is connected to outer sheath 11; a needle operating portion 22 that is connected to inner sheath 12 and is used for carrying out the operation of advancing and retracting puncture needle 13; pushing member handle 23 which is provided to the end of first pushing member 31 and is provided with rings on which the surgeon's fingers rest; and a pushing member knob 24 which is attached to the end of second pushing member 32.

Needle operating portion 22 is in the form of a cylinder with a base, and a knob 26 in which a groove is formed for the surgeon's fingers to rest is formed to end 22a which corresponds to this base part. Open end 22b is connected to inner sheath 12. Needle operating portion 22 has a gas port 25 on its lateral surface between end 22a and end 22b which is the flow introducing portion that is employed when gas is introduced into the space 28 that is formed inside puncture needle operating portion 22. First pushing member 31 and second pushing member 32 go through puncture needle operating portion 22 so as to pass through from end 22b to the opening 22c of end 22a. The air-tight state between opening 22c and first pushing member 31 is maintained by packing 27. As a result, there is no flow of gas from space 28 inside puncture needle operating portion 22. By relatively advancing or retracting puncture needle operating portion 22 with respect to holding member 21, puncture needle 13 can be advanced and retracted inside the body cavity with respect to outer sheath 11.

Pushing member handle 23 is attached to the outer periphery of first pushing member 31 which is pulled out from puncture needle operating portion 22. Locking member 17 can be pushed out from puncture needle 13 by pushing in pushing member handle 23 toward puncture needle operating portion 22. Pushing member knob 24 is attached to end 32b of second pushing member 32 which is pulled out from end 31b of first pushing member 31. Anchoring member 16 can be pushed out from puncture needle 13 by pushing in pushing member knob 24 toward pushing member handle 23 and puncture needle operating portion 22.

The gas relaying mechanism for supplying gas to gas port 25 will now be explained using FIG. 1. This gas relaying mechanism has an air pump 7 that suctions up air and then discharges it at a specific pressure. Electromagnetic valve 8a for selecting between relay and exhaust, a flow adjusting valve 8b for adjusting flow of the gas being relayed, and a flow meter 8c for monitoring the flow quantity of gas actually supplied, are connected in this order by tubing on the discharge side of air pump 7. Necessary commands are carried out by a CPU (central processing unit) 9. CPU 9 carries out switching of electromagnetic valve 8a and adjustment of the opening of flow adjusting valve 8b while receiving command signals to start or stop gas relay from a foot or hand switch, and while monitoring flow meter 8c. Note that flow meter 8c and gas port 25 are also connected with tubing.

Next, the sequence for suturing tissues such as internal organs with this anastomosing instrument 1 will be explained with suitable reference to FIGS. 1 through 3 and FIGS. 5, 6, and 7. Note that FIGS. 5 and 6 are figures for explaining the anastomosing procedure and the position of the pushing member at that time. FIG. 7 is a view for explaining the anastomosing procedure.

First, flexible endoscope 2 shown in FIG. 1 and inserted portion 10 of anastomosing instrument 1 shown in FIG. 2 are introduced into the body cavity. At this time, puncture needle operating portion 22 of hand operated portion 20 is pulled out from holding member 21 by a specific amount only, so that puncture needle 13 is housed inside outer sheath 11. Pushing member handle 23 is pulled out from puncture needle operating portion 22 by a specific amount only, so that first pushing member 31 is drawn back to a position in which it does not apply a pushing force on locking member 17, and has anchoring member 16 in a housed state therein. Pushing member knob 24 is pulled out from pushing member handle 23 by just a specific amount, so that second pushing member 32 is retracted back to a position that does not apply a pushing force on anchoring member 16 inside first pushing member 31.

From this state, the end of outer sheath 11 is moved to a position facing the biological tissue that is to be anastomosed, and puncture needle operating portion 22 is then pushed forward toward holding member 21 by a specific amount, thereby exposing puncture needle 13 from outer sheath 11. A foot or hand switch, not shown in the figures, is turned ON, and gas discharged by air pump 7 shown in FIG. 1 is directed to gas port 25. The gas directed to gas port 25 is introduced to inner sheath 12 of inserted portion 10 via the space 28 in the puncture needle operating portion 22 shown in FIG. 3. The gas passes through the clearance between first pushing member 31/inner sheath 12 and puncture needle 13, and the clearance between locking member 17 and puncture needle 13, and is discharged from opening 14 at the end of puncture needle 13. Note that locking member 17 is in contact with the inner wall of puncture needle 13 in the direction that is orthogonal to the longitudinal direction of puncture needle 13, so that locking member 17 does not fall out from puncture needle 13 during gas flow, etc.

When puncture needle operating portion 22 is pushed further in, puncture needle 13 penetrates the biological tissue of the organ while discharging gas from the end thereof. Gas is supplied from puncture needle 13, causing the organ to insufflate. Once it has been determined that a specific quantity of gas has been supplied and the organ has been insufflated to the extent necessary for the procedure, the foot or hand switch (not shown in the figures) is turned OFF and the supply of gas to gas port 25 is halted.

Figure 5A:
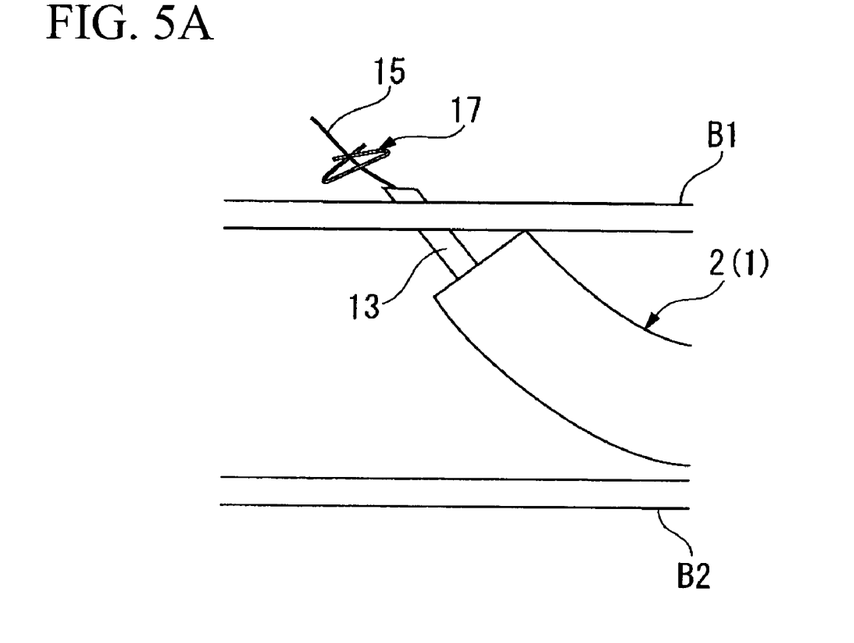
FIG. 5A is a view for explaining the anastomosing procedure.
Figure 5B:
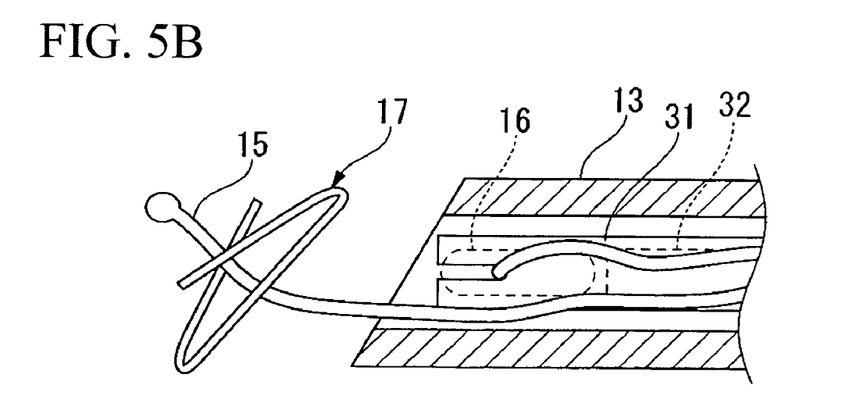
FIG. 5B is a view for explaining the positioning of the pushing members.

With the organ in an insufflated state, pushing member handle 23 shown in FIG. 3 is pushed toward puncture needle operating portion 22. As a result, the end of first pushing member 31 applies a pushing force on locking member 17 and locking member 17 is pushed out from opening 14 of puncture needle 13, as shown in FIG. 5B. As shown in FIG. 5A, locking member 17 is pushed out on the biological tissue B1 side which is to be anastomosed. Thus, when puncture needle operating portion 22 is pulled back from holding member 21, puncture needle 13 is retracted and is pulled out from biological tissue B1. As a result, suture material 15 is passed through biological tissue B1, while at the same time locking member 17 is retained in biological tissue B1. Since suture material 15 passes through the center of base 50 of locking member 17, base 50 comes into contact with biological tissue B1 when suture material 15 is pulled.

Figure 6A:
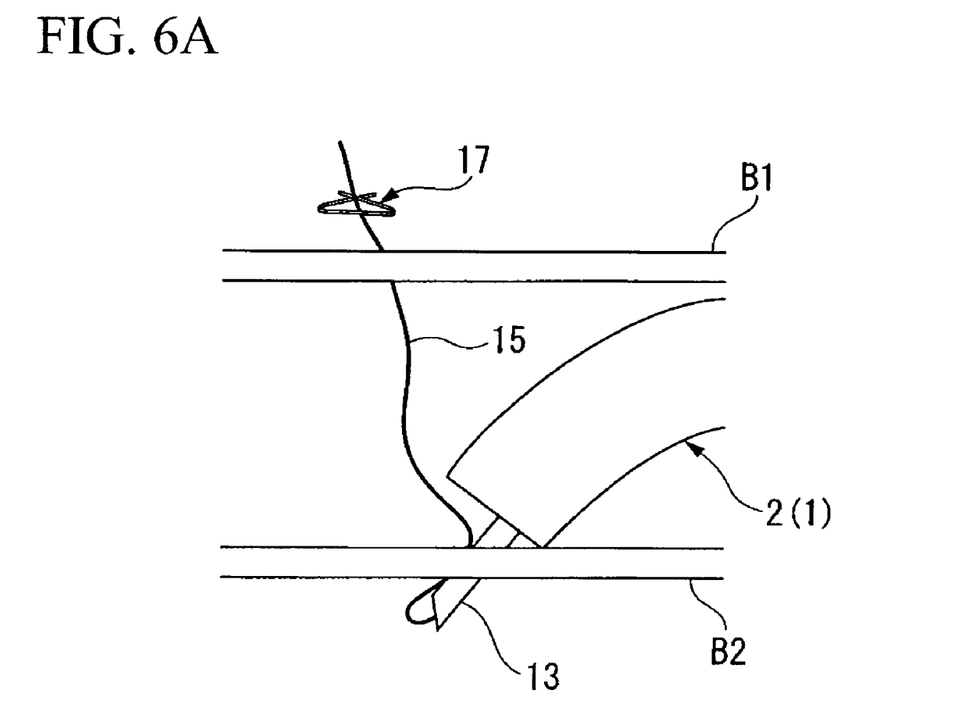
FIG. 6A is a view for explaining the anastomosing procedure.
Figure 6B:
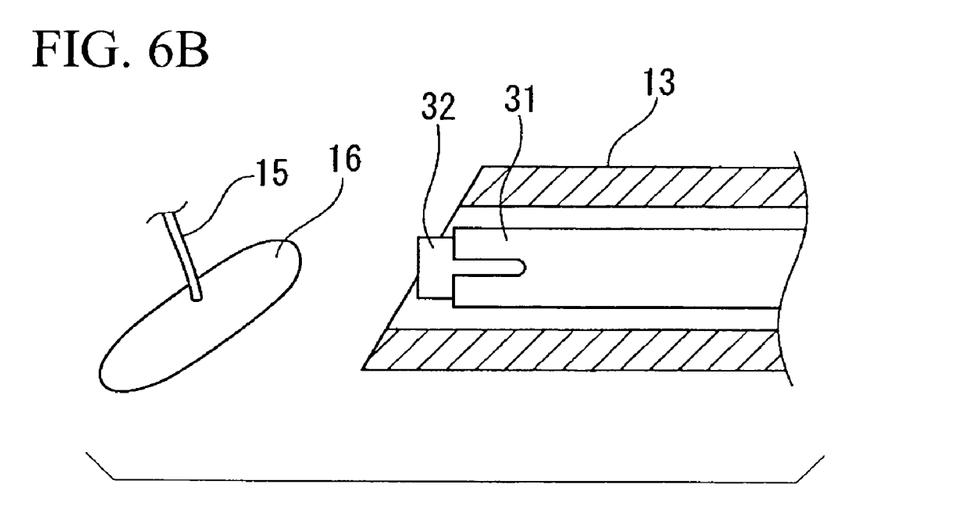
FIG. 6B is a view for explaining the positioning of the pushing members.

Next, in operating steps not shown in the figures, anastomosing instrument 1 is moved to a position facing biological tissue B2, and needle puncture operating portion 22 is pushed in with respect to holding member 21. As a result, puncture needle 13 penetrate biological tissue B2 as shown in FIG. 6A, as gas is being discharged from the end of puncture needle 13. When pushing member knob 24 (see FIG. 3) is pushed in toward pushing member handle 23, second pushing member 32 projects out more than the end of first pushing member 31, as shown in FIG. 6B, and anchoring member 16 which is housed in first pushing member 31 is pushed out from puncture needle 13. Thereafter, puncture needle operating portion 22 is pulled back to its original position, so that puncture needle 13 is pulled out from biological tissue B2.

Figure 7A:
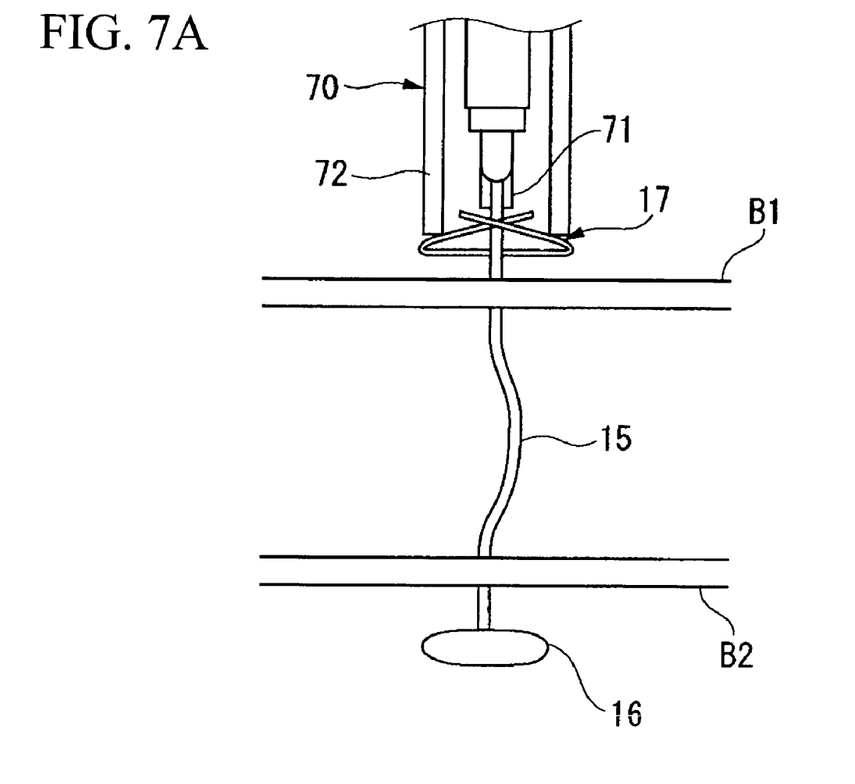
FIG. 7 is a view for explaining the anastomosing procedure.
Figure 7B:
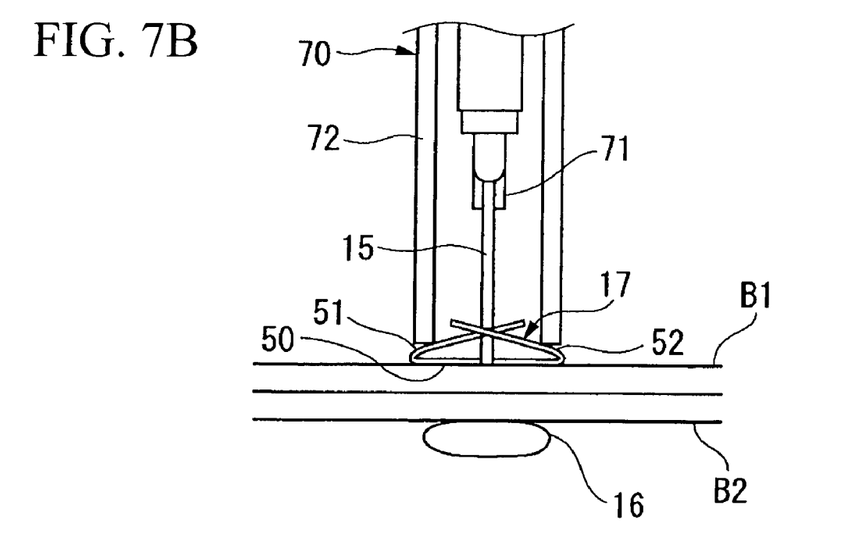

As a result, as shown in FIG. 7A, suture material 15 is passed through biological tissue B2, while at the same time anchoring member 16 is retained in biological tissue B2. The suture material 15 that extends from locking member 17 is gripped by another procedure instrument 70, which is provided with a forceps 71 housed inside a sheath 72. With locking member 17 being pushed by the end of sheath 72 so that base 50 comes into contact with biological tissue B1, suture material 15 is pulled so as to pull it through locking member 17. As disclosed above, this direction is that which widens the space between ends 51a,52a, thus locking member 17 permits movement of suture material 15. Accordingly, anchoring member 16, which is tethered to suture material 15, is pulled, which in turn pulls the biological tissue B2 that is in contact with anchoring member 16 toward the biological tissue B1 side. As a result, biological tissue B1 and biological tissue B2 are anastomosed as shown in FIG. 7B. Since locking member 17 has a wide area of contact with biological tissue B1 at this time, a reliable anchor effect is realized, and locking member 17 does not cut into biological tissue B1. Further, as disclosed above, when this locking member 17 moves in such a way that suture material 15 is directed from bent pieces 51,52 toward base 50, it acts to close the space between ends 51a,52a. Accordingly, biological tissue B1 and biological tissue B2 do not move in directions away from one another and suture material 15 does not move. Thus, there is no separation of the two anastomosed biological tissues B1 and B2.

Note that the present invention is not limited to the embodiments described above, but rather has a wide variety of applications.

Figure 8A:
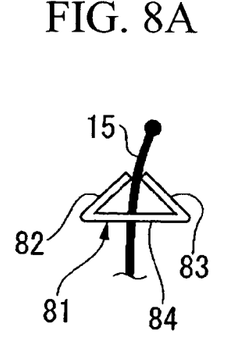
Figure 8B:
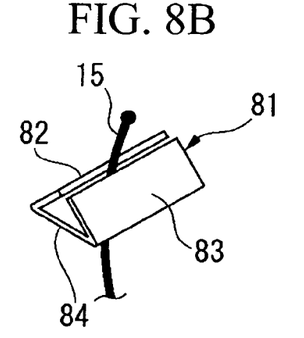

For example, locking member 17 may have the shape shown in FIG. 8. In the locking member 81 shown in FIGS. 8A and 8B, the directions of the short legs of a rectangular-shaped member may be bent in the same way, to form bent pieces 82,83. By passing suture material 15 between the ends of bent pieces 82 and 83, which have been brought close to one another, in a direction extending from the bending position of bent pieces 82,83 toward the ends, a locking mechanism for fastening and releasing suture material 15 in the same manner as disclosed above is realized. In this case, a base 84, which has a thin long shape and the largest area, serves as the contact surface that comes into contact with the biological tissue.

Figure 9A:
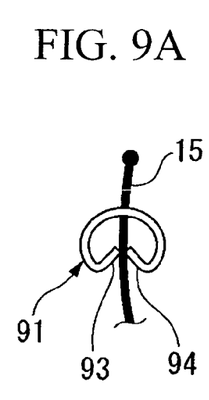
Figure 9B:
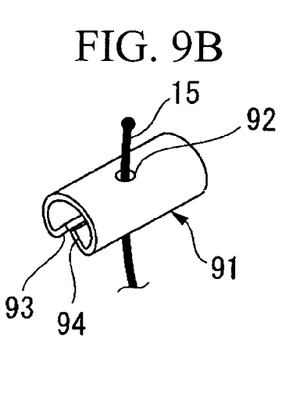

In the locking member 91 shown in FIGS. 9A and 9B, a hole 92 for passing suture material 15 is provided in the center of a narrow long member that is a circular arc in cross-section, and the ends that are orthogonal to the long side are bent in the direction of hole 92, to form bent pieces 93,94. In the case of this locking member 91 as well, by passing suture material 15 between the ends of bent pieces 93 and 94, which have been brought close to one another, in a direction extending from the bending position of bent pieces 93,94 toward the ends, a locking mechanism equivalent to that disclosed above is realized. The surface of this locking member 91 that is opposite hole 92 serves as the base, i.e., the contact surface that comes into contact with the biological tissue.

Figure 10:
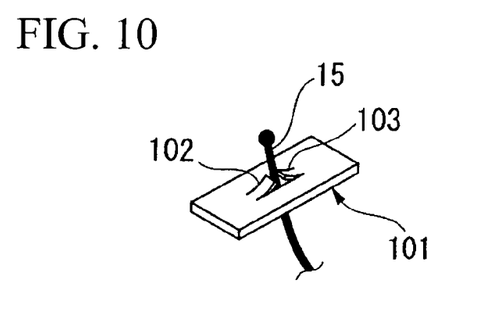
FIG. 10 is a perspective view of the locking member.

The locking member 101 shown in FIG. 10 has a shape in which a H-shaped cut-out is introduced at the center portion of the narrow long base, and bent pieces 102,103 are cut and raised. There is no hole such as described above. However, by passing suture material 15 between the ends of bent pieces 102 and 103, which have been inclined to be brought close to one another, in a direction extending from the bending position of bent pieces 102,103 toward the ends, a locking mechanism equivalent to that disclosed above is realized.

In this locking member 101, the portion that excludes bent pieces 102,103 serves as the base and is the contact surface that comes into contact with the biological tissue. Note that in each of the locking members 81, 91 and 101 shown in FIGS. 8 through 10, the contact surface is housed inside puncture needle 13 so as to be parallel to the axial direction thereof. Further, these locking members 81, 91 and 101 are disposed closer to the end of puncture needle 13 than anchoring member 16.

While the flow discharged from the end of puncture needle 13 may be air or another gas, a liquid such as physiologic saline is also acceptable.

As explained above, in the anastomosing instrument according to the first aspect of the invention, by disposing the surface of the locking member that is in contact with the biological tissue to be parallel to the axial direction of the puncture needle in the anastomosing instrument according to the present invention, the surface area of the locking member that is in contact with the biological tissue can be made larger, and the force for fixing the biological tissue in place can be increased. When anastomosing two biological tissues, the puncture needle first penetrates one of the biological tissues and the locking member is pushed out with the first pushing member. The suture material is then passed through this first biological tissue while the locking member is retained. Next, the puncture needle penetrates the other biological tissue, the anchoring member is pushed out with the second pushing member, and the suture material is passed through this other biological tissue while the anchoring member is retained. Accordingly, the locking member can be made larger than the anchoring member and the area that comes into contact with the biological tissue can be increased. As a result, the biological tissue can be anastomosed with surety.

In the anastomosing instrument according to the second aspect of the invention, by disposing the locking member to be closer to the end of the puncture needle than the anchoring member in this anastomosing instrument, the locking member can be made larger than the anchoring member, ensuring a large area of contact with the biological tissue. As a result, the biological tissue can be anastomosed with surety.

In the anastomosing instrument according to the third aspect of the invention, when the suture material is pulled in a direction that closes the space between the ends that are on either side of the suture material, or when the locking member is pushed toward the tissue to be anastomosed, the suture material is fastened between the ends, and relative movement of the locking member is prevented. On the other hand, when the suture material is pulled in a direction that widens the space between the ends, the ends release their fastening on the suture material, and movement of the locking member is permitted. Accordingly, it is possible to fasten the suture material and hold the anastomosed state using a simple structure.

The anastomosing instrument according to the fourth aspect of the invention penetrates biological tissue as flow is being discharged from the end of the puncture needle. As a result, it is possible to insufflate an organ, etc. during instrument penetration.

In the invention according to the fourth aspect, it is possible to insufflate the organ, etc. during needle penetration, so that it is possible to penetrate only the target tissue with surety and carry out the anastomosing procedure.

What is claimed:

1. An anastomosing device comprising:
   an anchoring member;
   a suture material, said anchoring member being attached to a first end of said suture material and being adapted to anchor in a biological tissue;
   a puncture needle;
   a locking member, through which a second end of said suture material is inserted and that comes into contact with the anastomosed biological tissue so as to prevent pull-out of the suture material, said anchoring member and said locking member being housed inside said puncture needle, wherein, once said puncture needle has passed through the biological tissues, said suture material is passed through the biological tissues as said anchoring member and said locking member are pushed out in accordance with operations from a hand held portion, thereby anastomosing said biological tissues, said locking member being disposed in the internal cavity of said puncture needle so that the surface of said locking member that is in contact with said biological tissue becomes parallel to the axial direction of said puncture needle;

a first pushing member that pushes out said locking member from said puncture needle; and a second pushing member that is housed inside said first pushing member and pushes out said anchoring member from said puncture needle;

wherein said locking member comprises a base and two bent pieces that are inclined with respect to said base so as to be opposite one another, said bent pieces being adapted such that the suture material that is passed between ends thereof is fastened when a force is applied so as to close the space between the opposing said ends, and the fastening of said suture material is released when a force is applied to as to widen the space between the opposing said ends, and wherein said locking member and said anchoring member are disposed substantially in line within said puncture needle such that said locking member is closer than said anchoring member relative to a piercing end of said puncture needle.

2. The anastomosing device according to claim 1, wherein a flow introducing portion on a side of said hand-held portion for supplying flow to the puncture needle is provided, and gas is discharged from a piercing end of said puncture needle.

3. The anastomosing device according to claim 1, wherein said base and said two bent pieces are formed in a single piece.

* * * * *